(12) United States Patent
Chiu et al.

(10) Patent No.: US 6,224,535 B1
(45) Date of Patent: *May 1, 2001

(54) RADIATION CENTERING CATHETERS

(75) Inventors: Jessica G. Chiu, Palo Alto; Eric D. Peterson, Fremont, both of CA (US)

(73) Assignee: Advanced Cardiovascular Systems, Inc., Santa Clara, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/024,666

(22) Filed: Feb. 17, 1998

(51) Int. Cl.$^7$ ............................. A61N 5/00; A61M 29/00
(52) U.S. Cl. ........................................................ 600/3
(58) Field of Search ............................... 600/1–8; 604/93, 604/171, 264, 280

(56) References Cited

U.S. PATENT DOCUMENTS

| | | |
|---|---|---|
| 4,581,017 | 4/1986 | Sahota . |
| 4,661,094 | 4/1987 | Simpson . |
| 4,697,575 | 10/1987 | Horowitz . |
| 4,706,652 | 11/1987 | Horowitz . |
| 4,744,366 | 5/1988 | Jang . |

(List continued on next page.)

FOREIGN PATENT DOCUMENTS

| | | |
|---|---|---|
| 9162312 | 2/1991 | (DE) . |
| 4315002 | 5/1993 | (DE) . |
| 0633041 | 7/1993 | (EP) . |
| 0688580 | 6/1994 | (EP) . |
| 0801961 | 4/1997 | (EP) . |

(List continued on next page.)

OTHER PUBLICATIONS

Weintraub et al., "Can Restenosis After Coronary Angioplasty Be Predicted From Clinical Variables", Journal of the American College of Cardiology, pp. 6–14, no. 1, Jan. 1993.

Kuntz et al., "Generalized Model of Restenosis after Conventional Balloon Angioplsty, Stenting and Directional Atherectomy", Journal of the American College of Cardiology, vol. 21, No. 1, pp. 15–25, Jan. 1993.

Haude et al., "Quantitative Analysis of Elastic Recoil after Balloon Angioplasty and after Intracoronary Implantation of Balloon-Expandable Palmaz–Schatz Stents", Jounral of the American College of Cardiology, pp. 26–34, vol. 21, No. 1, Jan. 1993.

Lindsay et al., "Aortic Arteriosclerosis in the Dog After Localized Aortic X–Irradiation", pp. 51–60, Circulation Research, vol. X, Jan. 1962.

(List continued on next page.)

*Primary Examiner*—Samuel Gilbert
(74) *Attorney, Agent, or Firm*—Blakely, Sokoloff, Taylor & Zafman, LLP

(57) ABSTRACT

The invention is directed to a radiation delivery catheter assembly for maintaining patency of a body lumen for a period of time sufficient to allow delivery of a radiation source to the body lumen. The catheter utilizes an inflatable region which maintains and centers the catheter in the body lumen. The catheter may include a perfusion lumen for supplying oxygenated blood to tissue located downstream from the catheter when the inflatable region is expanded in the body lumen. The inflatable region can be made up of a plurality of balloon segments which help center the radiation source, even if placed on a curved section of the body lumen. Embodiments of the invention include a catheter design which utilizes "rapid exchange" features and a dual therapeutic catheter which is capable of dilating a stenosed region of the body lumen prior to the administration of the radiation treatment. A two-piece protective sheath is used to protect the radiation source from bodily fluids.

50 Claims, 5 Drawing Sheets

U.S. PATENT DOCUMENTS

| | | |
|---|---|---|
| 4,748,982 | 6/1988 | Horzewski et al. . |
| 4,762,130 | 8/1988 | Fogarty et al. . |
| 4,763,671 | 8/1988 | Goffinet . |
| 4,771,777 | 9/1988 | Horzewski et al. . |
| 4,771,778 | 9/1988 | Mar . |
| 4,775,371 | 10/1988 | Mueller, Jr. . |
| 4,790,315 | 12/1988 | Mueller, Jr. et al. . |
| 4,815,449 | 3/1989 | Horowitz . |
| 4,861,520 | 8/1989 | Van't Hooft et al. . |
| 4,936,823 | 6/1990 | Colvin et al. . |
| 4,940,064 | 7/1990 | Desai . |
| 4,969,863 | 11/1990 | Van't Hooft et al. . |
| 4,976,720 | 12/1990 | Machold et al. . |
| 4,983,167 | 1/1991 | Sahota . |
| 4,994,560 | 2/1991 | Kruper, Jr. et al. . |
| 4,998,917 | 3/1991 | Gaiser et al. . |
| 5,002,560 | 3/1991 | Machold et al. . |
| 5,015,230 | 5/1991 | Martin et al. . |
| 5,019,042 | 5/1991 | Sahota . |
| 5,032,113 | 7/1991 | Burns . |
| 5,034,001 | 7/1991 | Garrison et al. . |
| 5,040,543 | 8/1991 | Badera et al. . |
| 5,046,503 | 9/1991 | Schneiderman . |
| 5,059,166 | 10/1991 | Fischell et al. . |
| 5,061,273 | 10/1991 | Yock . |
| 5,084,002 | 1/1992 | Liprie . |
| 5,100,429 | 3/1992 | Sinofsky et al. . |
| 5,133,956 | 7/1992 | Garlich et al. . |
| 5,137,513 | 8/1992 | McInnes et al. . |
| 5,176,617 | 1/1993 | Fischell et al. . |
| 5,176,661 | 1/1993 | Evard . |
| 5,180,368 | 1/1993 | Garrison . |
| 5,195,971 | 3/1993 | Sirhan . |
| 5,199,939 | 4/1993 | Dake et al. . |
| 5,213,561 | 5/1993 | Weinstein et al. . |
| 5,226,889 | 7/1993 | Sheiban . |
| 5,242,396 | 9/1993 | Evard . |
| 5,258,419 | 11/1993 | Rolando et al. . |
| 5,263,963 | 11/1993 | Garrison et al. . |
| 5,267,960 | 12/1993 | Hayman et al. . |
| 5,273,738 | 12/1993 | Matthews et al. . |
| 5,279,562 | 1/1994 | Sirhan et al. . |
| 5,282,781 | 2/1994 | Liprie . |
| 5,295,959 | 3/1994 | Gurbel et al. . |
| 5,295,960 | 3/1994 | Aliahmad et al. . |
| 5,295,995 | 3/1994 | Kleiman ............................ 604/96 X |
| 5,300,281 | 4/1994 | McMillan et al. . |
| 5,302,168 | 4/1994 | Hess . |
| 5,306,246 | 4/1994 | Sahatjian et al. . |
| 5,308,356 | 5/1994 | Blackshear, Jr. et al. . |
| 5,320,824 | 6/1994 | Brodack et al. . |
| 5,336,518 | 8/1994 | Narayanan et al. . |
| 5,350,361 | 9/1994 | Tsukashima et al. . |
| 5,352,199 | 10/1994 | Yower . |
| 5,354,257 | 10/1994 | Roubin et al. . |
| 5,380,747 | 1/1995 | Medford et al. . |
| 5,395,333 | 3/1995 | Brill ........................................ 604/96 |
| 5,405,622 | 4/1995 | Vernice et al. . |
| 5,409,495 | 4/1995 | Osborn . |
| 5,411,466 | 5/1995 | Hess . |
| 5,415,664 | 5/1995 | Pinchuk . |
| 5,441,516 | 8/1995 | Wang et al. . |
| 5,447,497 | 9/1995 | Sogard et al. . |
| 5,456,667 | 10/1995 | Ham et al. . |
| 5,458,572 | 10/1995 | Campbell et al. . |
| 5,484,384 | 1/1996 | Feamont . |
| 5,498,227 | 3/1996 | Mawad . |
| 5,503,613 | 4/1996 | Weinberger . |
| 5,503,614 | 4/1996 | Liprie . |
| 5,507,301 | 4/1996 | Wasicek et al. . |
| 5,507,769 | 4/1996 | Marin et al. . |
| 5,516,336 | 5/1996 | McInnes et al. . |
| 5,540,659 | 7/1996 | Teirstein . |
| 5,542,925 | 8/1996 | Orth . |
| 5,573,508 | 11/1996 | Thornton . |
| 5,573,509 | 11/1996 | Thornton . |
| 5,616,114 | 4/1997 | Thornton et al. . |
| 5,618,266 | 4/1997 | Liprie . |
| 5,643,171 | 7/1997 | Bradshaw et al. . |
| 5,653,691 | 8/1997 | Rupp et al. . |
| 5,668,486 | 11/1997 | Watson et al. . |
| 5,683,345 | 11/1997 | Waksman et al. . |
| 5,707,332 | 1/1998 | Weinberger ............................ 600/3 |
| 5,730,698 | 3/1998 | Fischell et al. . |
| 5,840,067 | 11/1998 | Berguer et al. . |
| 5,851,171 | 12/1998 | Gasson . |
| 5,871,436 | 2/1999 | Eury . |
| 5,910,101 | 6/1999 | Andrews et al. . |
| 5,938,582 | 8/1999 | Ciamacco, Jr. et al. . |

FOREIGN PATENT DOCUMENTS

| | | |
|---|---|---|
| 0829271 | 9/1997 | (EP) . |
| 0879614 | 5/1998 | (EP) . |
| 0865803 | 9/1998 | (EP) . |
| WO92/17236 | 3/1992 | (WO) . |
| WO93/04735 | 9/1992 | (WO) . |
| WO94/25106 | 5/1994 | (WO) . |
| WO95/19807 | 7/1995 | (WO) . |
| WO96/06654 | 8/1995 | (WO) . |
| WO96/10436 | 9/1995 | (WO) . |
| WO95/26681 | 10/1995 | (WO) . |
| WO96/19255 | 12/1995 | (WO) . |
| 96/10436 | 4/1996 | (WO) ....................................... 600/3 |
| WO96/14898 | 5/1996 | (WO) . |
| WO97/07740 | 8/1996 | (WO) . |
| WO97/37715 | 4/1997 | (WO) . |
| WO97/40889 | 4/1997 | (WO) . |
| WO98/01182 | 5/1997 | (WO) . |
| WO98/01183 | 7/1997 | (WO) . |
| WO98/01184 | 7/1997 | (WO) . |
| WO98/01185 | 7/1997 | (WO) . |
| WO98/39052 | 1/1998 | (WO) . |

OTHER PUBLICATIONS

Friedman et al., "The Antiatherogenic Effect of Iridium[192] Upon the Cholesterol–fed Rabbit", Journal of Clinical Investigation, pp. 185–192, vol. 43, No. 2, Feb. 1964.

Friedman et al., "Effect of Iridium 192 Radiation on Thromboatherosclerotic Plaque in the Rabbit Aorta", pp. 285–290, Archives of Pathology, vol. 80, Sep. 1965.

Hoopes et al. "Intraoperative Irradiation of the Canine Abdominal Aorta and Vena Cava", International Journal Radiation Oncology Biology, Physics vol. 13, No. 5, pp. 715–722, May 1987.

Weshler et al. "Inhibition by Irradiation of Smooth Muscle Cell Proliferation in the De–Endothelialized Rat Aorta", Frontiers in Radiation Biology, pp. 133–138, Oct. 1988.

Dawson, "Theoretic Considerationf Regarding Low–Dose Radiation Therapy for Prevention of Restenosis after Angioplasty", Texas Heart Institute Journal, vol. 18, No. 1, pp. 4–7, 1991.

Johnson et al., "Review of Radiation Safety in the Cardiac Catheterizatio Laboratory", Radiation Safety, Catheterization and Cardiovascular Diagnosis, pp. 186–194, 1992.

Schwartz et al. "Effect Beam Irradiation on Neointimal Hyperplasia After Experimental Coronay Artery Injury", Journal of the American College of Cardiology, vol. 19, No. 5, pp. 1106–1113 Apr. 1992.

March et al., "8–Methoxypsoralen and Longwave Ultraviolet Irradiation are a Novel Antiproliferative Combination for Vascular Smooth Muscle", Circulation, vol. 87, No. 1, pp. 184–191, Jan. 1993.
Hunink et al., "Risks and Benefits of Femoropopliteal Percutaneous Balloon Angioplasty", Journal of Vascular Surgery, pp. 183–194, vol. 17, No. 1, Jan. 1993.
American College of Cardiology, pp. 26–34, vol. 21, No. 1, Jan. 1993.
Schwartz et al., "Differential Neointimal Response to Coronary Artery Injury in Pigs and Dogs", Arteriosclerosis and Thrombosis, pp. 395–400, vol. 14, No. 3, Mar. 1994.
Liemann et al., "Prophylactic Endovascular Radiotherapy to Prevent Intimal Hyperplasia after Stent Implantation in Femoropopliteal Arteries", CardioVascular and Interventional Radiology, pp. 12–16, 1994.
Wiedemann et al., "Effects of High–Dose Intracoronary Irradiation on Vasomotor Function and Smooth Muscle Histopathology", Intracoronary Irradiation and Vasomotion, The American Physiological Society, pp. H–125–H132, 1994.
Wagner et al., "Potential Biological Effects Following High X–Ray Dose Interventional Procedures", Journal of Vascular and Interventional Radiology, pp. 71–84, vol. 5, No. 1, Jan.–Feb. 1994.
Wiedmann et al., "Intracoronary Irradiation Markedly Reduces Restenosis after Balloon Angioplasty in a Porcine Model", Journal of the American College of Cardiology, pp. 1491–1498, vol. 23, No. 6, May 1994.
Kakuta et al., "Differences in Compensatory Vessel Enlargement, Not Intimal Formation, Account for Restenosis After Angioplasty in the Hupercholesterolemic Rabbit Model", Circulation, pp. 2809–2815, vol. 89, No. 6, Jun. 1994.
Fischell et al., "Low Dose β–Particle Emission From 'Stent'Wire Results in Complete, Localized Inhibition of Smooth Muscel Cell Proliferation", Basic Science Reports, Circulation, pp. 2956–2863, vol. 90, No. 6, Dec. 1994.
Waksman et al., "Endovascular Low–Dose Irradiation Inhibits Neointima Formation after Coronary Artery Balloon Injury in Swine", Circulation, pp. 1533–1539, vol. 91, No. 5, Mar. 1, 1995.
Wiedermann et al., "Intracoronary Irradiation Markedly Reduces Neointimal Proliferation After Balloon Angioplasty in Swine: Persistent Benefit at 6–Month Follow–Up", Journal of the American College of Cardiology, pp. 1451–1456, vol. 25, No. 6, May 1995.
Waksman et al., "Intracoronary Radiation Before Stent Implantation Inhibits Neointima Formation in Stented Porcine Coronary Arteries", Brief Rapid Communications, Circulation, pp. 1383–1386, vol. 92, No. 6, Sep. 15, 1995.
Verin et al., "Intra–Arterial Beta Irradiation Prevents Neointimal Hyperplasia in a Hypercholesterolemic Rabbit Restenosis Model", Circulation, pp. 2284–2290, vol. 92, No. 8, Oct. 15, 1995.
Waksman et al., "Intracoronary Low–Doseβ–Irradiation Inhibits Neointima Formation After Coronary Artery Balloon Injury in the Swine Restenosis Model", Circulation, pp. 3025–3031, vol. 92, No. 10, Nov. 15, 1995.
Herhrlein et al., "Radioactive Stents", Department of Cardiology, Discoveries in Radiation for Restenosis, pp. 63–64, Abstract 22, Jan. 1996.
Fischell et al., "A Beta–Particle Emitting Radioisotope Stent for the Prevention of Restenosis", Discoveries in Radiation for Restenosis, Abstract 23, p. 65, Jan. 1996.
Li et al., "A Novel Brachyehtapy Source for Treament of Coronary Artery Restenosis", Discoveries in Radiation for Restenosis, Abstract 24, pp. 67–72, Jan. 1996.

Waksman, "Catheter–Based Radiation in Stented Arteries", Discoveries in Radiation for Restenosis, Abstract 25, pp. 73–74, Jan. 1996.
Martin, "Radiation For Peripheral Applications: Technical Aspects", Discoveries in Radiation for Restenosis, Abstract 27, pp. 81–82, Jan. 1996.
Lumsden et al., "Restenosis in Peripheral Vascular Disease", Discoveries in Radiation for Restenosis, Abstract 28, pp. 83–88, Jan. 1996.
Schopohl et al., "Endovascular Irradiation for Avoidance or Recurrent Stenosis After Stent Implantation in Peripheral Arteries–5 Years Follow–Up", Discoveries in Radiation for Restenosis, Abstract 29, pp. 89–92, Jan. 1996.
Waksman, "Radiation in the Peripheral System at Emory", Discoveries in Radiation for Restenosis, Abstract 30, pp. 93–94, Jan. 1996.
Teirstein, et al., "Catheter–Based Radiation Therapy to Inhibit Restenosis Following Coronary Stenting", Discoveries in Radiation for Restenosis, p. 99, Abstract 31, Jan. 1996.
King, "Clinical Restenosis Trials Using Beta Energy Radiation", Discoveries in Radiation for Restenosis, Abstract 32, pp. 101–102, Jan. 1996.
Urban et al., "Endovascular Irradiation With 90Y Wire", Discoveries in Radiation for Restenosis, Abstract 33, pp. 103–104, Jan. 1996.
Condado et al., "Late Follow–Up after Percutaneous Transluminal Coronary Angioplasty (PTCA) and Intracoronary Radiation Therapy (ICRT)", Discoveries in Radiation for Restenosis, Abstract 34, p. 105, Jan. 1996.
Weldon, "Catheter Based Beta Radiation System", Discoveries in Radiation for Restenosis, Abstract 35, p. 111, Jan. 1996.
Van't Hooft et al., "HDR Afterloader for Vascular Use", Discoveries in Radiation for Restenosis, p. 113, Abstract 36, Jan. 1996.
Fischell et al., "The Radioisotope Stent: Conception and Implementation", Discoveries in Radiation Restenosis, p. 115, Abstract 37, Jan. 1996.
Youri Popowski et al., "Radioactive Wire In a Self–Centering Catheter System", Discoveries in Radiation Restenosis, pp. 117–118, Abstract 38, Jan. 1996.
Richard V. Calfee, "High Dose Rate Afterloader System for Endovascular Use–Neocardia", Discoveries in Radiation Restenosis, p. 119, Abstract 39, Jan. 1996.
Smith, "Issues on Handling Radioactive Devices to Prevent Restenosis", pp. 121–122, Abstract 40, Jan. 1996.
Unterberg, "Reduced Acute Thrombus Formation Results in Decreased Neointimal Proliferation After Coronary Angioplasty", Journal of the American College of Cardiology, pp. 1747–1754, vol. 26, No. 7, Dec. 1995.
Schwartz et al., "Effect of External Beam Irradiation on Neointimal Hyperplasia After Experimental Coronary Artery Injury", Journal of the American College of Cardiology, pp. 1106–1113, vol. 19, No. 5, Apr. 1992.*
Hehrlein et al., "Low Dose Radioactive Endovascular Stents Prevent Smooth Muscle Cell Proliferation and Neointimal Hyperplasia in Rabbits", Circulation, pp. 1570–1575, vol. 92, No. 6, Sep. 15, 1995.*
PCT Search Report PCT/US 99/03327 mailed Jun. 18, 1999.
PCT Search Report PCT/US 99/03329 mailed Jun. 18, 1999.
PCT Search Report PCT/US 99/03328 mailed Jun. 18, 1999.
PCT Search Report PCT/US 99/03360 mailed Jun. 17, 1999.
PCT Searchg Report PCT/US 99/03343 mailed Jun. 17, 1999.

* cited by examiner

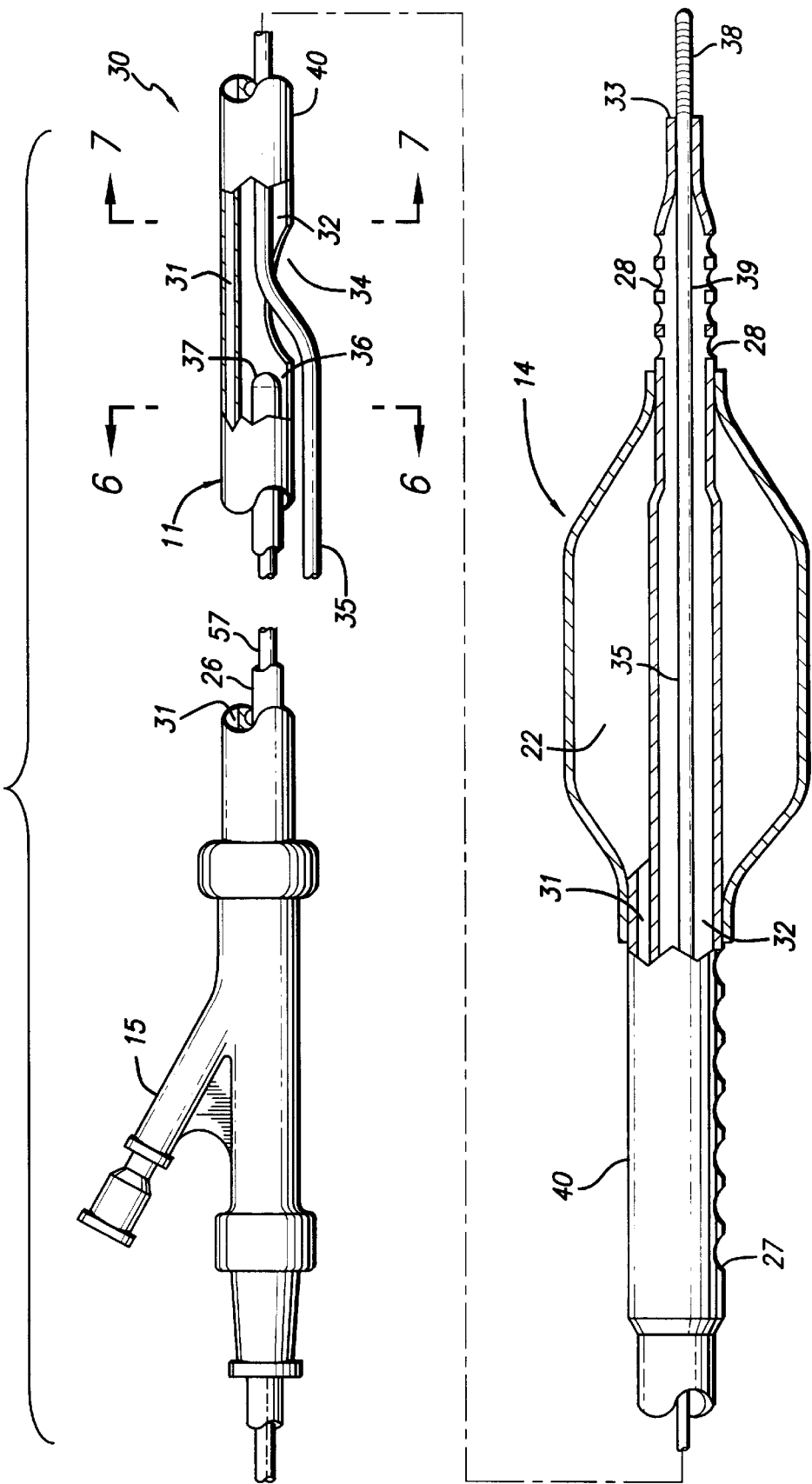

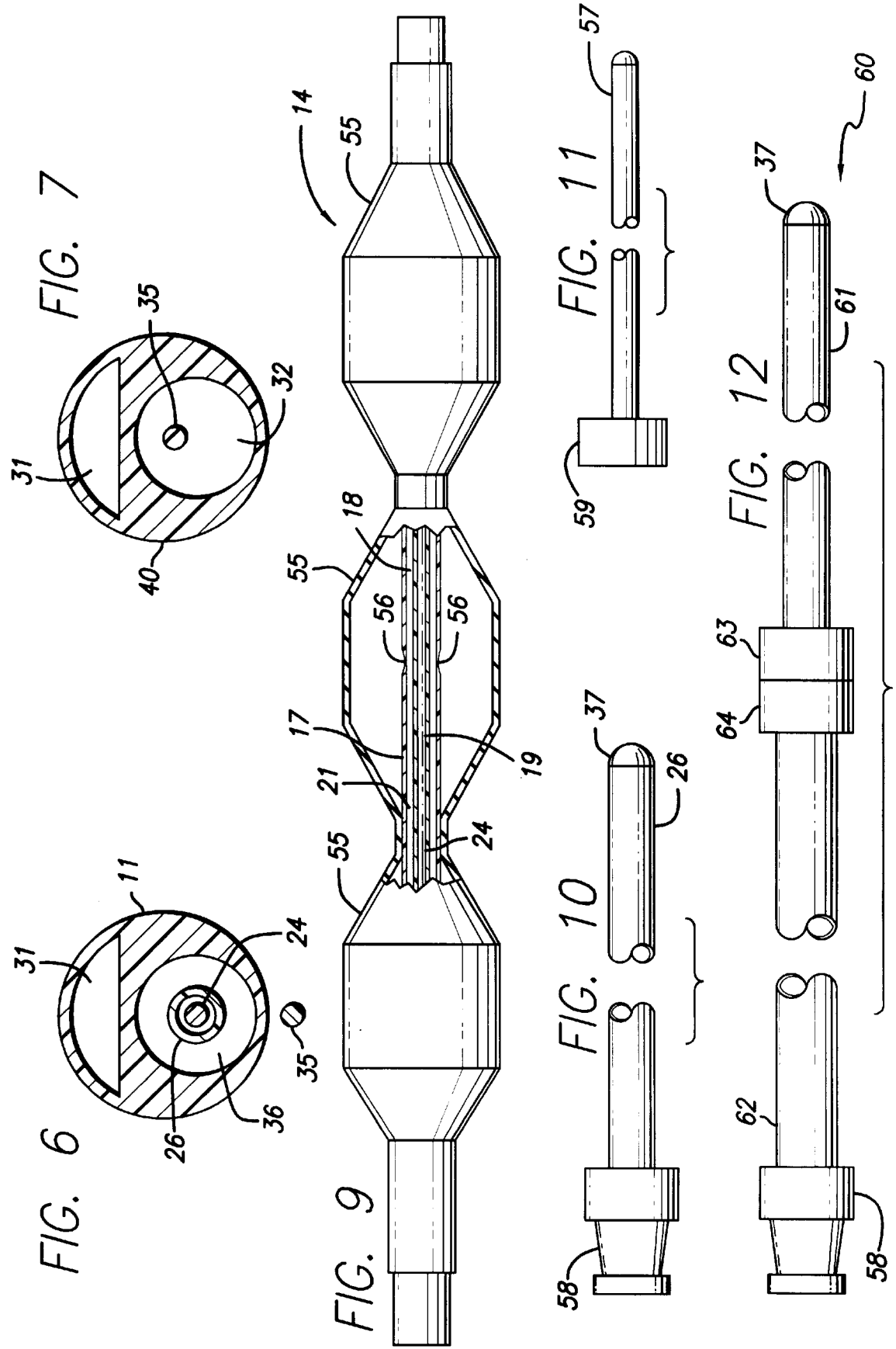

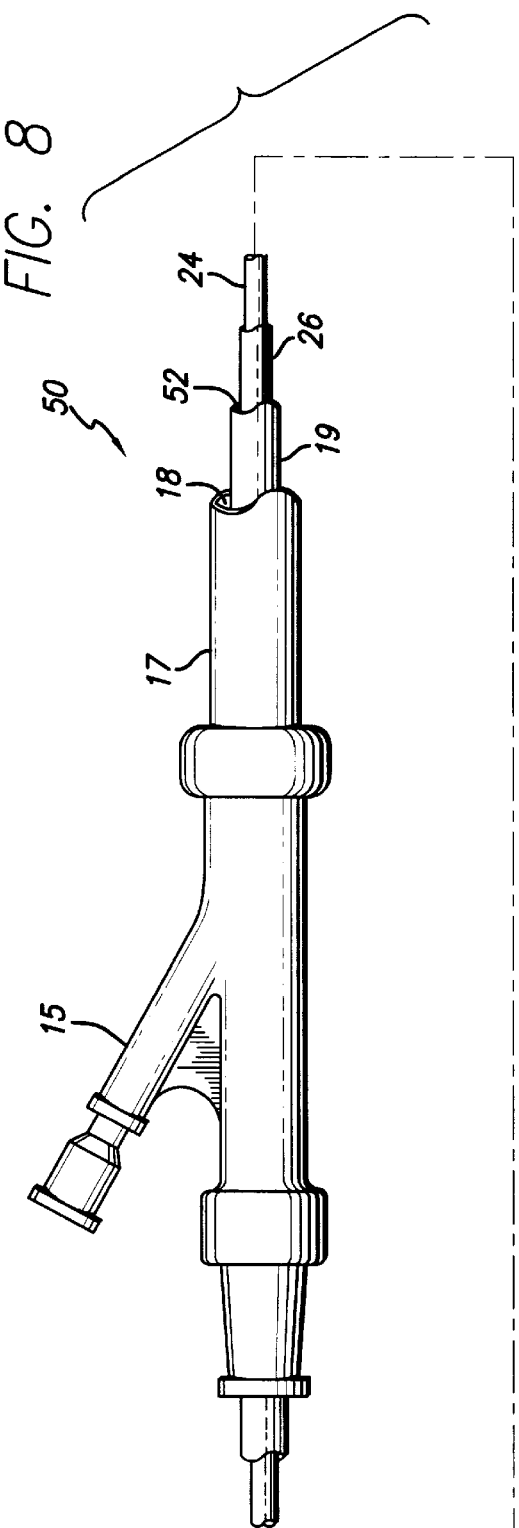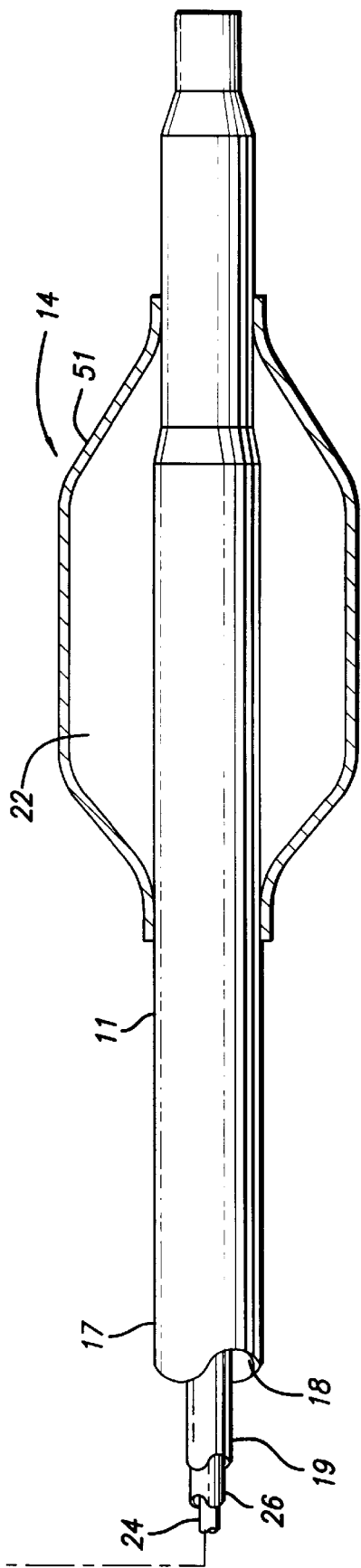
FIG. 8

RADIATION CENTERING CATHETERS

BACKGROUND OF THE INVENTION

This invention generally relates to intravascular catheters and particularly to intravascular catheter assemblies for delivering radiation treatment to a body lumen while providing blood perfusion through the body lumen past the catheter while the radiation treatment is being administered.

In percutaneous transluminal coronary angioplasty (PTCA) procedures, a guiding catheter having a preshaped distal tip is percutaneously introduced into the cardiovascular system of a patient through the brachial or femoral artery and is advanced therein until the preshaped distal tip is disposed within the aorta adjacent to the ostium of the desired coronary artery. The guiding catheter is then twisted and torqued from its proximal end to turn its distal tip so that it can be guided into the coronary ostium. In an over-the-wire dilatation catheter system, a guide wire and a dilatation catheter having an inflatable balloon on the distal end thereof are introduced into, and advanced through, the proximal end of the guiding catheter to the distal tip of the guiding catheter seated within the coronary ostium. The distal tip of the guide wire is usually manually shaped (i.e. curved) by the physician or one of the attendants before it and the dilatation catheter are introduced into the guiding catheter. The guide wire is usually first advanced out of the distal end of the guiding catheter and is maneuvered into the patients coronary vasculature containing the stenosis to be dilated, and is then advanced beyond the stenosis. Thereafter, the dilatation catheter is advanced over the guide wire until the dilatation balloon is position across the stenosis. Once the dilatation catheter is in positioned, the balloon of the catheter is filled with radiopaque liquid at relatively high pressures (e.g., generally about 4–12 atmospheres) to inflate it to a predetermined size (preferably the same as the inner diameter of the artery at that particular location) in order to radially compress the atherosclerotic plaque of the stenosis against the inside of the wall of the artery, thereby increasing the diameter of the occluded area. The balloon can then be deflated so that the catheter can be removed and blood flow resumed through the dilated artery.

One common problem that sometimes occurs after an angioplasty procedure has been performed is the development of restenosis at, or near, the original site of the stenosis. When restenosis occurs, a second angioplasty procedure or even bypass surgery may be required, depending upon the degree of restenosis. In order to reduce the likelihood of the development of restenosis and thereby prevent the need to perform bypass surgery or subsequent angioplasty procedures, various devices and procedures have been developed for preventing restenosis after arterial intervention. For example, an expandable cage (commonly termed "stent") designed for long term implantation with the body lumen has been utilized to help prevent the occurrence of restenosis.

More recent devices and procedures for preventing restenosis after arterial intervention employ the use of a radiation source to inhibit the proliferation of smooth muscle cells which are believed to be the primary cause of restenosis. Balloon catheters have been used to deliver and maintain the radiation source in the area where arterial intervention has taken place, exposing the area to a sufficient radiation dose to abate cell growth. Two such devices and methods are described in U.S. Pat. No. 5,302,168 (Hess) and U.S. Pat. No. 5,503,613 (Weinberger). Other devices and methods which utilize radiation treatment delivered by an intravascular catheter are disclosed in commonly-owned and assigned co-pending application U.S. Ser. No. 08/654,698, filed May 29, 1996, entitled Radiation-Emitting Flow-Through Temporary Stent and co-pending application Ser. No. 08/705,945, filed Aug. 29, 1996 now U.S. Pat. No. 5,782,740, entitled Radiation Dose Delivery Catheter with Reinforcing Mandrel, which are incorporated herein by reference. Another medical device for the treatment of a body vessel by radiation is disclosed in European Patent App. 0 688 580 A1 (Schneider).

One problem common to many of the balloon catheters which provide radiation treatment to a particular part of a patient's vascular system is that it is sometimes preferable to treat the target area with a lower dose rate, delivering the desired therapeutic dose over a longer period of time, rather than a higher dose rate over a shorter period of time. If conventional balloon catheters are utilized to center the radiation source in the artery, then the inflated balloon will inhibit or restrict the flow of blood through the artery, which can pose serious risk of damage to tissue downstream from the occluded portion of the artery since the tissue will be deprived of oxygenated blood. As a result, the time in which the balloon can remain expanded within the artery would be diminished, effecting the time period in which the radiation dosage can be maintained in the area of the artery where restenosis may occur. Thus, a higher radiation dose rate may have to be used due to the occlusion of the vessel caused by the inflated balloon catheter, which again, may not be as advantageous as providing a lower dose rate.

What has been needed and heretofore generally unavailable in catheters which provide treatment of the body vessel with a radiation source is an intravascular catheter assembly which allows delivery of a radiation source to the area where restenosis may occur for a period of time sufficient to kill the cells and prevent development of restenosis while allowing blood to perfuse pass the occluded region during the radiation procedure. Such an intravascular catheter should be flexible so that it can be expanded on a curved portion of a body lumen, such as a coronary artery, while properly centering and maintaining the radiation source wire within the body lumen. Additionally, such an intravascular catheter would have to be relatively easy and inexpensive to manufacture, have an expandable region that is strong and reliable under pressure, and capable of being formed in a variety of shapes to allow flexibility in the amount and pattern of expansion and deformation of the expandable region. The present invention satisfies these and other needs as will be described hereinafter.

SUMMARY OF THE INVENTION

The present invention is directed to radiation centering catheter assemblies having an inflatable region located at the distal end of an elongated catheter body which can hold open a body lumen for a sufficient period of time to permit delivery of a radiation source to a body lumen while permitting perfusion of oxygenated blood past the inflatable region to tissue located downstream from the catheter. The catheter assemblies may be configured to several popular catheter designs including, but not limited to, over-the-wire, rapid exchange, and multi-lumen designs which are known in the art.

The radiation centering catheter in accordance with the present invention includes an elongated catheter body having proximal and distal ends, a guide wire lumen extending at least partially through the elongated catheter body and an inflatable region located near the distal end of the elongated catheter body which is in fluid communication with an inflation lumen that extends from the proximal end of the elongated catheter body.

The inflation region is configured to be flexible so that it can be expanded on a curved portion of a body lumen, such as a coronary artery. It is also capable of centering a radiation source within the body lumen, even if the inflatable region is positioned on a curved section of the body lumen. The inflation region performs all of these features while still allowing blood to flow through it (via a perfusion lumen) to supply oxygenated blood to tissue downstream from the catheter when the inflated region is in its expanded position.

In an "over-the-wire" embodiment of the present invention, the radiation centering catheter allows for an over-the-wire delivery and advancement thereof of the elongated catheter body (via a separate guide wire) to a location within a body lumen where the radiation dose is to be administered. A guide wire lumen is used both for advancing the elongated catheter body along the guide wire to the target area and for advancing a radiation source wire to target area as well. After the catheter is in place in the target area with the inflatable region inflated to its expanded position, the guide wire is removed from the guide wire lumen allowing the radiation source wire to be advanced to the target area. The exchange may be performed by first placing a protective sheath into the guide wire lumen utilizing a support mandrel to advance the sheath into its proper position within the guide wire lumen. Thereafter, the support mandrel can be removed to allow the radiation source wire to be advanced from the radiation source storage facility (commonly referred to as an afterloader) through the protective sheath to the target area. Once the radiation source wire has been positioned to provide the necessary radiation dosage, the inflatable region can be deflated to its original unexpanded state and the catheter, protective sheath and radiation source wire can then be removed from the patient's vasculature.

In one particular embodiment of the present invention, a portion of the elongated catheter body is made using a multiple lumen arrangement wherein one lumen is utilized to inflate the inflatable region and a second lumen is utilized as the guide wire lumen. In this particular embodiment, a plurality of perfusion ports which are in fluid communication with the guide wire lumen, or another available lumen, are placed proximally and distally of the inflatable region to create a perfusion lumen which provides oxygenated blood to tissue downstream of the inflatable region. As a result, the radiation centering catheter can remain in the body lumen for a longer period of time, thus increasing the duration of the radiation treatment.

In a "rapid-exchange" embodiment of the present invention, the radiation centering catheter utilizes rapid exchange technology to provide a delivery path for the catheter and radioactive source, while properly centering the catheter and radiation source within a lesion for a period of time sufficient to permit delivery of the radiation treatment to the body lumen. This "rapid exchange" type catheter has a relatively short guide wire receiving sleeve or lumen (sometimes referred to as a "rail") extending a short distance through the distal portion (usually through the inflatable region) of the catheter body. This rail portion preferably extends approximately 10 cm, and typically about 30 to 40 cm, from a first guide wire port at a distal end of the catheter to a second side guide wire port located on the elongated catheter body. This particular radiation centering catheter can be advanced within the patient's vascular system in much the same fashion as described above, as the short rail portion of the catheter slides along the length of the guide wire. Alternatively, the guide wire may be first advanced within the patient's vasculature until the distal end of the guide wire extends distally to the stenosis with the catheter then being mounted onto the proximal end of the in-place guide wire and advanced over the guide wire until the inflatable region is positioned across the stenosis. This particular structure allows for the rapid exchange of the catheter usually without the need for an exchange wire or adding a guide wire extension to the proximal end of the guide wire.

In this rapid-exchange embodiment of the present invention, the elongated catheter body includes a main inner lumen which extends from its proximal end to the "rail" portion of the catheter body to allow the radiation source wire and protective sheath to be advanced from its proximal end for placement in the target area where the radiation treatment is to be administered. Since this particular embodiment utilizes a rapid-exchange design, the guide wire only utilizes the rail portion of the elongated catheter body for advancement of the catheter within the patient's vasculature. In actual use, a support mandrel and protective sheath can be advanced through the main inner lumen to a location adjacent to the rail portion of the catheter body near the proximal side guide wire port. There, the tip of the protective sheath can be used as a guide wire "exit ramp" to prevent the guide wire from advancing past the side guide wire port into the main inner lumen of the elongated catheter body.

Once the catheter has been advanced into the target region of the patient's vasculature, the guide wire can be removed from the rail portion, allowing the protective sheath to be advanced into the rail portion and into the target area. By preloading the protective sheath within the catheter body, the time required for loading and advancing the protective sheath is reduced. Once the protective sheath is in place, the radiation source wire can be advanced from an afterloader through the protective sheath to the target area.

In another preferred embodiment of the present invention, the radiation centering catheter utilizes an over-the-wire design consisting of a coaxial catheter body with an inflatable region mounted at the distal tip. This radiation centering catheter utilizes an inner tubular member which extends coaxially within an outer tubular member to define an annular inflation lumen which extends from the proximal end of the elongated catheter body to the inflatable region. A source for providing inflation fluid to the inflatable region is in fluid communication with the annular inflation lumen to inflate or deflate the inflatable region as may be required. The internal lumen of the inner tubular member can be used both as a guide wire lumen for facilitating the advancement of the catheter body to, and through, the stenosis and also for advancing the protective sheath and radiation source wire to the target area. This particular embodiment provides dual therapeutic features since the inflatable region can be made with a sufficiently strong balloon material which can be used both to perform the PTCA procedure and later to center and maintain the radiation source wire within the body lumen during the radiation treatment phase of the procedure. Alternatively, this dual therapeutic radiation centering catheter could be constructed utilizing a multilumen design which allows perfusion ports to be in fluid communication with an available lumen to create a perfusion lumen to provide oxygenated blood to tissue downstream from the expanded inflatable region. This perfusion lumen can be quite useful since it could be used both during the initial PTCA procedure and later when the radiation treatment is being administered to the patient.

Generally, the inflatable region is made from an inflatable balloon, such as those used in conventional dilatation catheters. However, in one particular embodiment of the present invention, the inflatable region can be formed from a series of short balloons which are individually formed and attached to the elongated catheter body. These individual balloon segments assist in the centering the radiation source wire, especially when the target area is at a curved portion of the patient's vasculature. The elongated catheter body includes an inner lumen which allows the entire catheter to be advanced to the target area via a guide wire. The radiation source wire and protective sheath can be advanced to the target area through this lumen as well. These individual balloon segments also can be used in conjunction with an elongated catheter body having multiple lumens including a perfusion lumen to provide blood perfusion past the catheter once the balloon segments are inflated within the body lumen.

A presently preferred embodiment of the protective sheath is described herein with an associated support mandrel which is utilized to advance the protective sheath within the inner lumen of the catheter body to the target area. The distal end of the protective sheath includes a non-traumatic soft tip which helps prevent injury to tissue should the tip come in contact with the body lumen. The proximal end includes an adapter which can be connected to a radiation afterloader.

In another particular embodiment, a composite protective sheath can be formed utilizing two individual sections of sheathing materials. The distal section can be made from a thin wall tubing having greater flexibility and a proximal section made from a thicker wall tubing for providing a stronger barrier of protection against possible radiation exposure to the personnel handling the radiation source wire. These distal and proximal sections can be connected together using an appropriate fastener, such as a lure fitting. By utilizing a two-piece construction, the length of the support mandrel can be reduced since the distal section can first be advanced to the target area using a shorter support mandrel and thereafter attached to the proximal section. The proximal end of the proximal section can then be attached to the afterloader for advancing the radiation source wire through this composite protective sheath.

These and other advantages of the invention will become more apparent from the foregoing detailed description thereof when taken in conjunction with the accompanying exemplary drawings.

BRIEF DESCRIPTION OF THE DRAWINGS

FIG. 5 is an elevational view, partially in cross-section, of another embodiment of a radiation centering catheter embodying features of the present invention.

FIG. 6 is a cross-sectional view of the radiation centering catheter of FIG. 5 taken along lines 6—6.

FIG. 7 is a cross-sectional view of the radiation centering catheter of FIG. 5 taken along lines 7—7.

FIG. 8 is an elevational view, partially in cross-section, of another embodiment of a radiation centering catheter having dual therapeutic capabilities which also embodies features of the present invention.

FIG. 9 is an elevational view, partially in cross-section, of a series of short balloon segments which form an inflatable region that can be utilized with the radiation centering catheters described herein.

FIG. 10 is an elevational view of a protective sheath embodying features of the present invention.

FIG. 11 is an elevational view of a support mandrel which can be utilized to advance a protective sheath used in accordance with the present invention.

FIG. 12 is an elevational view of a two-piece protective sheath embodying features of the present invention.

DETAILED DESCRIPTION OF THE PREFERRED EMBODIMENTS

Figure 1:
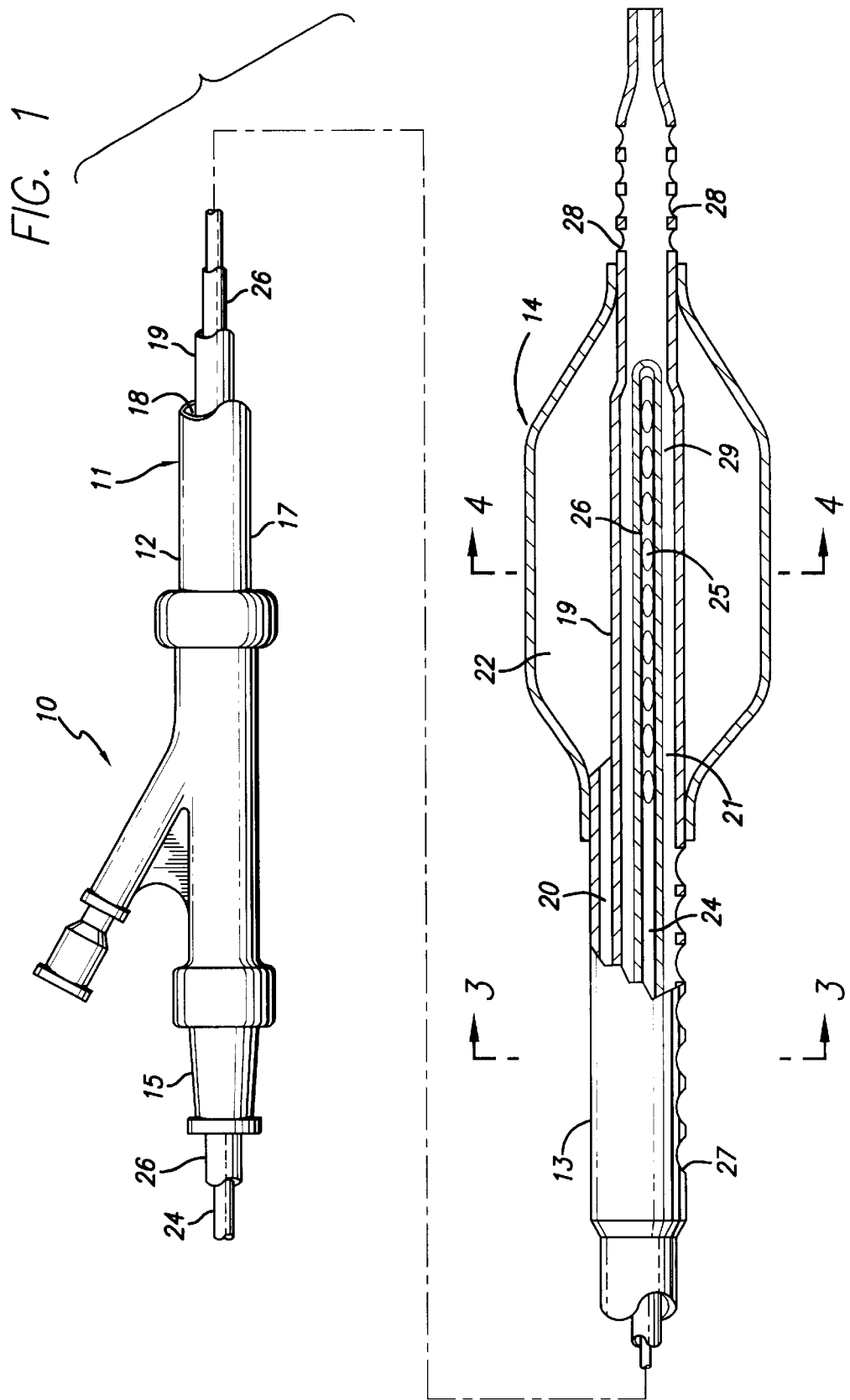
FIG. 1 is an elevational view, partially in cross-section, of a radiation centering catheter embodying features of the present invention.

The present invention provides a radiation centering catheter assembly for delivering and maintaining a low dose radiation source to a patient's body lumen, such as a coronary artery or other vessel, for an extended period of time. The catheter assembly permits perfusion of blood during the radiation therapy and will center the radiation source so that equal amounts of radiation will be applied to the artery. While the invention is described in detail as applied to the coronary arteries, those skilled in the art will appreciate that it can also be used in other body lumens as well, such as peripheral arteries and veins. Where different embodiments have like elements, like reference numbers have been used.

FIGS. 1–4 illustrate a radiation centering catheter assembly 10 embodying features of the present invention. The catheter assembly 10 generally includes an elongated catheter body 11 having a proximal high strength coaxial section 12 and a distal multilumen section 13, with an inflatable region 14, such as an inflatable balloon, located on the distal multilumen section of the catheter body. An adapter 15 is provided at the proximal end of the proximal coaxial section 12 to direct inflation fluid from a high pressure source such as a syringe pump (not shown) to the interior of the inflatable region 14.

The proximal coaxial section 12 of the elongated catheter body 11 is formed from an inner tubular member 19 which extends coaxially within an outer tubular member 17 to form an annular inflation lumen 18 which is adapted to direct inflation fluid from the adaptor to the interior of the inflatable region. This annular inflation lumen 18 extends from the proximal end of the catheter body to the distal multilumen section 13. The inner tubular member 19 has an inner lumen 21 which also extends from the proximal end of the catheter body to this distal multilumen section 13. There, the coaxial arrangement of the proximal section 12 translates to the multilumen design of the distal section 13.

Figure 3:
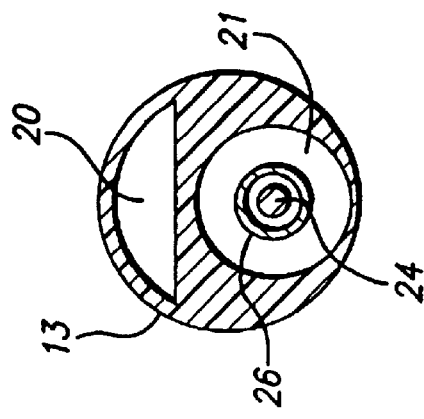
FIG. 3 is a cross-sectional view of the radiation centering catheter of FIG. 1 taken along lines 3—3.

This distal multilumen section 13 of the catheter body 11, as illustrated in FIG. 3, has two inner lumens 20 and 21 extending therein. The first inner lumen 20 is an inflation lumen having a D-shaped transverse cross-sectional shape which is in fluid communication with the annular inflation lumen 18 and is generally axially aligned therewith. This first inner lumen 20 is in turn in fluid communication with the interior of the inflatable region 14. The resulting arrangement of the annular inflation lumen 18 and first inner lumen 20 creates a continuous inflation lumen which can facilitate the rapid transfer of inflation fluid to and from the interior 22 of the inflatable region 14.

The second inner lumen 21 of the distal section 13 has a circular transverse cross-sectional shape and is connected to the inner tubular member 19 of the proximal section 12. The inner lumen 21 creates a guide wire lumen which continuously extends from the proximal to distal ends of the elongated catheter body 11. A guide wire (not shown) would be slidably disposed within the guide wire lumen to facilitate the advancement and replacement of the catheter assembly 10 within the artery 23 of a patient.

Figure 2:
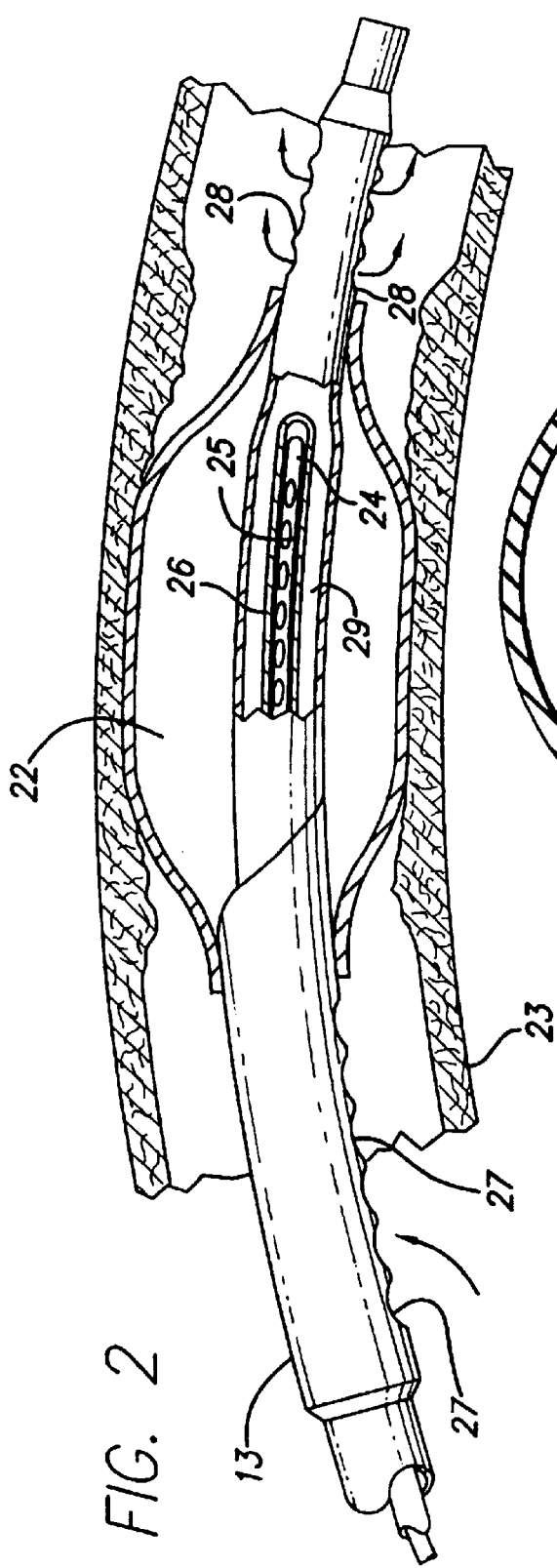
FIG. 2 is a cross-sectional view of the inflatable region of the radiation centering catheter of FIG. 1, showing the inflatable region in its expanded position within a curved section of an artery where radiation treatment is to be provided.
Figure 4:
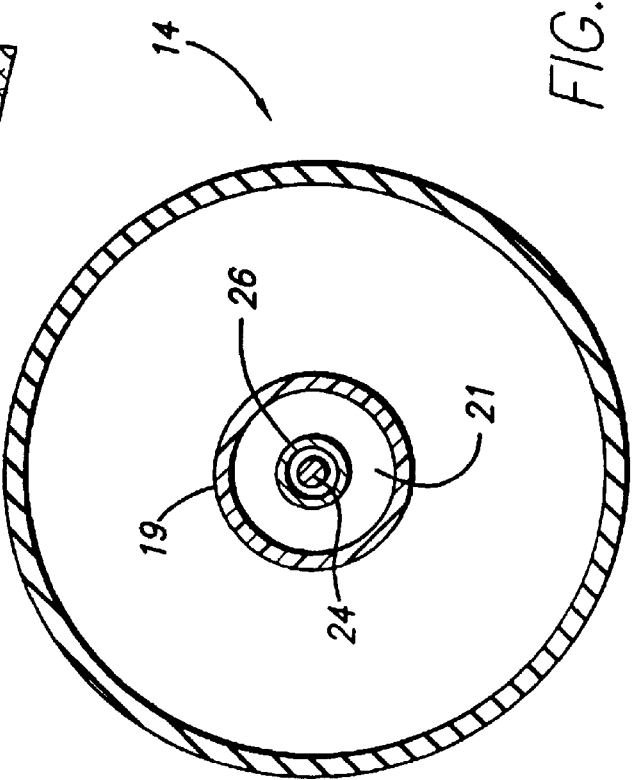
FIG. 4. is a cross-sectional view of the radiation centering catheter of FIG. 1 taken along lines 4—4.

As can be seen in FIGS. 1 and 2, once the catheter assembly 10 has been positioned within the artery 23, the guide wire (not shown) can be removed from the composite guide wire lumen, allowing a radiation source wire 24 to be inserted into the guide wire lumen for a period of time sufficient to provide the radiation dosage to the body lumen. Preferably, the radiation source wire 24 is hollow at its distal end and contains a radiation dose in the form of a radiation source 25, such as pellets, radiation gas or radioactive liquid or paste. The radiation source wire 24 may also have a radioactive source coated at its distal end. This radiation source wire 24 provides the proper dosage of radiation to the areas of the artery 23 where arterial intervention has been performed, either by PTCA, atherectomy, stenting or other means to help abate the proliferation of smooth muscle cells in this region. A protective sheath 26, which encases the radiation source wire 24, seals the radiation source 25 from exposure to bodily fluids, such as blood, and provides a sterile barrier between the radiation source wire 24 (which can be reusable and non-sterile) and the patient's vascular system. It is preferable that the radiation source wire 24 be stored and its deployment controlled by an afterloader (not shown) which is known in the art.

Again referring to FIGS. 1 and 2, the catheter assembly 10 includes a plurality of proximal perfusion ports 27 located on the distal multilumen section 13 and in fluid communication with inner lumen 21, ports 27 being placed proximal to the inflatable region 14. Similarly, a plurality of distal perfusion ports 28 located on the distal multilumen section 13 of the catheter body are placed distal to the inflatable region 14. These particular perfusion ports 27 and 28 are in fluid communication with the second inner lumen 21 to create a perfusion lumen 29 which permits blood to flow through the catheter when the inflatable region 14 is expanded during the radiation therapy. It should be appreciated that additional perfusion ports and perfusion lumens could also be provided to increase the blood flow past the inflatable region during the treatment. By utilizing perfusion lumens, the radiation centering catheter can be maintained in the artery for a much longer period of time thereby eliminating or preventing ischemia during the radiation treatment.

In practice, once the catheter assembly 10 has been placed within the vasculature of the patient, the guide wire can be removed from the composite guide wire lumen to allow the protective sheath 26 to be loaded into the guide wire lumen, utilizing a support mandrel, such as the one shown in FIG. 11. Once the protective sheath 26 has been properly placed within the guide wire lumen, the support mandrel can be removed from the proximal end of the catheter assembly. The radiation source wire 24 can then be advanced through the protective sheath 26 from the afterloader to the target area where the radiation therapy is to be provided. It is noted that reference herein to the "target area" means that part of the body lumen that has received a PTCA, atherectomy, or similar procedure to reduce or remove a stenosis, which is subject to the development of restenosis caused, in part, by intimal hyperplasia or the proliferation of smooth muscle cells.

Once the required period of time for radiation treatment has been completed, the inflatable region 14 can be deflated, allowing the entire catheter assembly, radiation source wire and protective sheath to be removed from the body lumen. It should be appreciated that the proximal end of the protective sheath 26 can be connected to an afterloader where the radiation source wire may be stored during the initial set up procedure while the catheter assembly is being positioned into the target area. Thereafter, the radiation source wire can be advanced from the afterloader through the protective sheath, which prevents or reduces possible exposure of the radiation source to personnel performing the radiation treatment. Similarly, a two-piece protective sheath such as the one shown in FIG. 12 and described hereinafter could be utilized to help prevent possible exposure of the radiation source to the personnel handling the radiation source wire.

FIGS. 5–7 illustrate a radiation centering catheter assembly 30 which utilizes rapid-exchange technology for delivering and maintaining a low dosage radiation source to the patient's body lumen. The catheter assembly 30 generally includes an elongated catheter body 11 and an inflatable region 14 which is shown in this particular embodiment as an inflatable balloon. An adapter 15 is located on the proximal end of the elongated catheter body 11. An inflation lumen 31 extends along a substantial portion of the elongated catheter body 11 and is in fluid communication with the interior 22 of the inflatable region 14.

The elongated catheter body 11 includes a guide wire lumen 32 positioned in the distal portion of the elongated catheter body 11 which extends from a first guide wire port 33 located at the distal end of the elongated catheter body 11 and a second guide wire port 34 located in the sidewall of the elongated catheter body 11. Both of these guide wire ports 33 and 34 are in fluid communication with the guide wire lumen 32 and with the guide wire lumen 32 define a "rail" segment 40 of the catheter (also referred to as a "sleeve") which generally extends through the inflatable region 14, although it is possible to utilize a much shorter rail which can be located distal to the inflatable region 14. A guide wire 35 is slidably disposed within this relatively short guide wire lumen 32 to facilitate the rapid advancement or placement of the catheter assembly 30. Further details of rapid exchange catheters can be found in U.S. Pat. Nos. 5,458,613; 5,180,368; 5,496,346; 5,061,273; and 4,748,982, which are incorporated herein by reference.

The elongated catheter body 11 includes a plurality of proximal perfusion ports 27 located proximal to the inflatable region 14 and a plurality of distal perfusion ports 28 which are placed distal to the inflatable region 14. These perfusion ports 27 and 28 are in fluid communication with the guide wire lumen 32 to create a perfusion lumen which permits blood to flow through the guide wire lumen 32 when the inflatable region 14 is inflated allowing oxygenated blood to be supplied to tissue located downstream from the catheter during the radiation treatment.

The elongated catheter body 11 includes a main inner lumen 36 which extends from its proximal end to the second guide wire port 34. As can be seen in FIG. 5, a protective sheath 26 and support mandrel 57 are preloaded into the main lumen 36 of the elongated catheter body 11 to a location where the tip 37 of the protective sheath 26 is adjacent to the second side guide wire port 34. This tip 37 of the protective sheath 26 creates an incline or ramp at the second guide wire port 34 which can be used as a guide wire "exit ramp" to prevent the guide wire from advancing past the second guide wire port 34 and into the main inner lumen 36 when the guide wire is being loaded on the rail portion 40 of the catheter. Such an arrangement facilitates the insertion or withdrawal of the guide wire 35 through the guide wire lumen 32. Additionally, preloading of the protective sheath 26 into the elongated catheter body reduces the time needed for inserting the protective sheath into the main lumen 36 of the elongated catheter body 11.

The guide wire 35, which is slidably disposed within the guide wire lumen 32, has a coil 38 on its distal end which is shown in FIG. 5 extending out of the first guide wire port 33 and an elongated core member 39 which is shown extending out of the second guide wire port 34, as would be utilized in a rapid exchange mode.

In the embodiment shown in FIGS. 5–7, the distance between the distal end of the inflatable region 14 to the first guide wire port 33 can be about 3 to 5 cm, but not greater than 60 cm, and preferably from about 20 to about 50 cm, so that when the inflatable region is expanded within the patient's vascular system, the second guide wire port 34 will remain within the interior of a guiding catheter to ensure that the guide wire 35 does not have an opportunity to form a loop when the entire catheter assembly 30 is pulled back into the guiding catheter.

When the catheter assembly 30 has been properly positioned within an artery of a patient, the guide wire 35 can be removed from the guide wire lumen 32 and the protective sheath 26 can be advanced into the guide wire lumen 32 to the target area where the radiation treatment is to be provided. This can be done by pushing the support mandrel forward to move the protective sheath into the rail portion of the elongated catheter body and into the target area. Thereafter, the support mandrel can be removed, allowing the radiation source wire to be advanced through the protective sheath from an afterloader. Once the radiation treatment has been completed, the inflatable region can be deflated, allowing the entire catheter assembly, radiation source wire and protective sheath to be removed from the body lumen.

In another preferred embodiment of the invention, as shown in FIG. 8, the radiation centering catheter assembly 50 comprises a dual therapeutic catheter which is capable of dilating a stenosis within the body lumen. After the stenosis has been dilated, the catheter can remain within the artery to center the radiation source wire. The catheter assembly 50 is shown utilizing a coaxial design having an elongated catheter body 11 which includes an inflatable region 14, such as an inflatable balloon 51, located on the distal portion thereof and an adapter 15 on the proximal end thereof. An inner tubular member 19 extends coaxially within an outer tubular member 17 and defines an annular inflation lumen 18 which extends from the proximal end of the elongated catheter body 11 to the inflatable region 14. The interior 22 of the inflatable balloon 51 is in fluid communication with a source of inflation fluid, such as a high pressure syringe (not shown) at the proximal end of the catheter assembly 50. The distal end of the inner and outer tubular members 19 and 17 are joined together by suitable means such as adhesive or heat bonding to seal the inflation lumen 18.

The elongated catheter body 11 includes a guide wire lumen 52 positioned in the distal portion of the elongated catheter body 11 which extends from the proximal to the distal end of the elongated catheter body 1. A guide wire (not shown) would be slidably disposed within the guide wire lumen 52 to facilitate the advancement or replacement of the catheter assembly 50 within the artery of the patient. As can be seen in FIG. 8, a radiation source wire 24 and protective sheath 26 can also be advanced within the guide wire lumen 52 for treatment in the target area.

The inflatable balloon 51 of the catheter assembly 50 is capable of first dilating the stenosis in the target area where radiation treatment will be later provided. The inflatable balloon 51 can be made from an inelastic (non-distensible) material which is capable of compressing the plaque buildup which forms the stenosis in the patient's vascular system. Once the dilatation process has been performed in the target area, the catheter assembly 50 can remain within the patient's vasculature to allow the radiation source wire to be inserted for immediate radiation therapy. As a result, there is no need to exchange a PTCA dilatation catheter with a centering catheter.

It should be appreciated that although the catheter assembly 50 shown in FIG. 8 utilizes a coaxial construction, it is also possible to utilize a multilumen design which provides a separate inflation lumen for inflating the balloon 51 and a main lumen which functions as a guide wire lumen. This main lumen could also be utilized to receive the radiation source wire and protective sheath when radiation treatment is to be provided. By utilizing a multilumen design, the guide wire lumen could also include perfusion ports both proximal and distal to create a perfusion lumen to permit blood perfusion both during the dilatation of the stenosis and afterwards during radiation treatment. Thus, this catheter assembly 50 can remain within the patient's body lumen for an extended period of time.

In practice, once the catheter assembly 50 has been placed within the vasculature of the patient, the inflatable balloon 51 can be inflated to compress the buildup of plaque in the target area. It should be appreciated that in accordance with established procedures known in the art, the inflatable balloon may have to be inflated to higher pressures in order to properly compress the plaque buildup in the target area. Once the patient's vasculature has been properly dilated, the guide wire can be removed from the guide wire lumen to allow the protective sheath 26 to be loaded into the guide wire lumen utilizing a support mandrel (such as the one shown in FIG. 11). Once the protective sheath has been properly placed within the guide wire lumen, the support mandrel can then be removed from the proximal end of the catheter assembly. The radiation source wire can then be advanced through the protective sheath from afterloader to the target area where the radiation therapy is to be provided. Once the required period of time for treatment has been completed, the inflated balloon can be deflated, allowing the entire catheter assembly, radiation source wire and the protective sheath to be removed from the body lumen. Again, it should be appreciated that the proximal end of the protective sheath can be connected to an afterloader where the radiation source wire may be stored during the initial setup procedure when the catheter assembly is positioned in the target area. Thereafter, the radiation source wire can be advanced from the afterloader through the protective sheath to the target area, preventing or reducing possible exposure of the radiation source to personnel performing the radiation procedure.

Referring now to FIG. 9, one particular embodiment of an inflatable region 14 which can be utilized with any of the catheter assemblies herein described is shown. The inflatable region 14 consists of a plurality of individual balloon sections 55 which help center the catheter shaft, assuring that an equal amount of radiation dosage is provided within the body lumen. These individual balloon sections 55 also assist in the centering of the balloon and radiation source wire when the target area is at a curved portion of the patient's vasculature, again helping to maintain an equal dosage of radiation to the body lumen. These individual balloon sections 55 can be made from a single balloon which is divided into the individual sections by the use of collars or other restraining members which could be placed along the length of the balloon to form the individual balloon sections. Alternatively, a series of short balloons may be formed individually and heat sealed (or adhesively attached) to the catheter shaft without the need for collars. Still another option is to form a series of short balloons on a single tubing, which can then be appropriately sealed to the catheter shaft. The proximal and distal ends of each balloon can be bonded (heat, adhesive, etc.) to the distal end of outer member 17.

Still referring to FIG. 9, the inflatable region 14 is shown utilizing a coaxial construction in which an inner tubular member 19 extends coaxially within an outer tubular member 17 to define an annular inflation lumen 18 which extends to each of the balloon sections to inflate and deflate the individual lumen sections as may be needed. Openings 56 formed in the outer tubular member 17 would be needed to maintain the interior of a balloon section in fluid communication with the annular inflation lumen. As is shown in FIG. 9, a radiation source wire 24 is shown disposed in a guide wire lumen 18 of the inner tubular member 19. A protective sheath, which normally would accompany the radiation source wire, is not shown for clarity.

Alternatively, a multilumen design could be utilized in conjunction with the balloon segments shown in FIG. 9 without departing from the spirit and scope of the present invention. For example, one lumen could be utilized as an inflation lumen with a second lumen being utilized as the guide wire/radiation source wire lumen in a similar fashion as the other multilumen catheters herein described. A plurality of perfusion ports could be placed proximally and distally to the balloon segments to create a perfusion lumen which allows oxygenated blood to flow through the guide wire lumen when the balloon sections are inflated within the patient's artery. As a result, the time in which the balloon segments can remain expanded within the artery would increase, allowing additional time for the radiation treatment to be administered to the patient. It should be appreciated that the individual balloon segments 55 shown in FIG. 9 could be used in conjunction with any catheter assembly which embodies features of the present invention.

Referring now to FIGS. 10 and 11, a protective sheath 26 and a support mandrel 57 are shown in greater detail. The protective sheath 26 is shown as a thin wall tubing having a non-traumatic soft tip 37. The proximal end of the protective sheath 26 is connected to an adapter 58, which can be connected to a fitting on the radiation afterloader.

Referring specifically to FIG. 11, the support mandrel 57 consists of an extruded filament made from Teflon, polyethylene ethyl ketone (PEEK) or other similar material having sufficient axial strength to move the protective sheath 26 into the inner lumen of the catheter assembly. A knob 59 is attached to the proximal end of the mandrel 57 to allow the user to easily manipulate the device during use.

Referring now to FIG. 12, a composite protective sheath 60 utilizing a two-piece design includes a distal section 61 and a proximal section 62. This distal section 61 is made from a thin wall tubing and is approximately 140 to 170 cm from end to end. This distal section 61 has a soft non-traumatic tip 37 located at its distal end and a lure fitting 63 located at its proximal end. The proximal section 62 is attached to the distal section 61 by another lure fitting 64 located at the distal end of the proximal section 62. An adapter 58 is located at the proximal end of the proximal section 62 which can be connected to the radiation afterloader. This proximal section 62 is made from a thicker wall tubing such as Teflon or PE and is approximately 100 cm in length. It should be appreciated that only the distal section 61 is loaded into the catheter assembly with the proximal section 62 being connected only after the distal section 61 has been properly placed within the catheter assembly. The thicker wall tubing of this proximal section 62 helps reduce possible exposure of the radiation source to the personnel handling the radiation source wire. It should be appreciated that the use of a two-piece protective sheath 60 is advantageous since the person advancing this protective sheath does not have to utilize the longer protective sheath and mandrel shown in FIGS. 10 and 11. Rather, the user advances the shorter distal section into the guide wire lumen of the catheter assembly utilizing a shorter support mandrel. Once the distal section 61 is in place, the two lure fittings 62 and 64 are connected to form the larger sheath which can then be connected to the afterloader. Once the radiation treatment has been completed, the distal sheath 61 could be easily removed with the catheter assembly and radiation source wire.

Generally, the dimensions of the catheter assembly of the present invention are essentially the same dimensions of vasculature used in angioplasty procedures. The overall length of the catheter may be about 100 to 175 cm when a Seldinger approach through the femoral artery is employed. The diameter of the catheter body may range from about 0.30 to 0.065 inches. The inflatable region in its unexpanded condition has approximately the same diameter as the catheter body, but may be expanded to a maximum diameter of about one to about 5 mm for coronary arteries and substantially larger (e.g., 10 mm) for peripheral arteries. The diameter of the guide wire lumen should be sufficiently larger than the diameter of the guide wire to allow the catheter to be easily advanced and removed from the guide wire. Additionally, the diameter of the guide wire lumen should be sufficiently larger than the diameter of the radiation source wire and protective sleeve to allow these two devices to be easily advanced and removed from within the guide wire lumen.

In use, the inflatable region is held in its expanded condition for a time sufficient to allow the radiation dosage to effect those cells which would otherwise cause restenosis to develop. Preferably, a sufficient dose of radiation can be delivered from about one minute to about sixty minutes to prevent development of restenosis. In its expanded condition, the inflatable region presses against, or at least comes in close proximity to, the walls of the artery and in doing so centers the radiation source wire within the artery. Centering of this radiation source wire is important so that all portions of the artery receive as close to uniform and equal amounts of radiation as possible. Also, centering helps prevent radiation burns or hot spots from developing on portions of the target area.

The catheter assemblies of the invention as described herein are generally employed after an atherectomy, percutaneous transluminal coronary angioplasty procedure, or stent implantation to allow the radiation dose to be administered to an area where restenosis might otherwise develop within a coronary artery. It should be recognized by those skilled in the art that the catheter of the present invention can be used within a patient's vasculature system after vascular procedures other than a PTCA, stent implantation or atherectomy have been performed.

The catheter assembly of the present invention may be formed from conventional materials of construction which are described in detail in prior art patents referenced herein. The materials forming the catheter body and protective sheath can be made out of relatively inelastic materials, such as polyethylene, polyvinyl chloride, polyesters and composite materials. The various components may be joined by suitable adhesives such as the acrylonitrile based adhesive sold as Loctite 405. Heat shrinking or heat bonding may also be employed when appropriate. Additionally, the present invention can be made with a material to form the balloon and balloon segments that is elastic (distensible) if compression of plaque is not required. An elastic material such as latex would be suitable for use. When using the dual therapeutic catheter assembly, a suitably strong balloon material should be used since compression of the plaque would be required. Conventional balloon materials used in dilatation catheters would be suitable for use with this dual therapeutic catheter. The radiation source wire can be made from materials such as stainless steel, titanium, nickel titanium and platinum nickel alloys, or any NiTi alloys, or any polymers and composites. Variations can be made in the composition of the materials to vary properties.

As described herein, the radiation centering catheter assembly will deliver a low dosage of radiation through the body lumen, such as a coronary artery, and is configured to provide the dosage over longer periods of time if necessary, due to the catheter's ability to allow blood to perfuse past the inflatable region during treatment. It is preferred that a low dosage of radiation, on the order of about 0.1 up to about 3.0 curies be the typical radiation dose provided to treat, for example, a coronary artery. Preferably, 1 to 2 curies will provide a proper dosage level.

The radiation delivered to a coronary artery should be in the range from about 20 to 3,000 rads in preferably not less than thirty seconds. The radiation dose can be delivered in less than thirty seconds, however, it is preferable that a longer time frame be used so that a lower dose can be administered in the target area.

It is contemplated that different radiation sources be used, and the preferred radiation sources include iridium$^{192}$ if gamma radiation is used, and phosphorus$^{32}$ if beta particles are used. Further, it is contemplated that the radiation sources may provide beta particles or gamma rays to affect the target cells. However, alpha emitting radiation sources also can be used even though such radiation does not travel very far in human tissue. The use of beta and gamma emitting radiation sources is well known for treating and killing cancerous cells.

Other modifications can be made to the present invention without departing from the spirit and scope thereof. The specific dimensions, doses, times and materials of constructions are provided as examples and substitutes are readily contemplated which do not depart from the invention.

What is claimed is:

1. A radiation centering catheter assembly for maintaining the patency of a body lumen for a period of time sufficient to permit delivery of a radiation dose to the body lumen while permitting blood perfusion, comprising:

an elongated catheter body having a proximal end and a distal end;

an inflation lumen extending within the elongated catheter body to a location within a distal portion of the elongated body;

an inflatable region located near the distal end of the elongated catheter body having an interior in fluid communication with the inflation lumen, the inflatable region adapted to be expandable to contact a portion of the body lumen;

a perfusion lumen extending through a portion of the elongated catheter body for permitting perfusion of blood through the inflatable region when the inflatable region is expanded within the body lumen;

a guide wire lumen extending through at least a portion of the elongated catheter body for receiving a guide wire;

a radiation source wire; and a protective sheath adapted to encase the radiation source wire, the protective sheath and the radiation source wire being insertable within the guide wire lumen to provide a radiation source to the body lumen.

2. The catheter of claim 1, wherein the inflatable region is made from a plurality of inflatable balloon segments extending axially along the elongated catheter body.

3. The catheter as defined in claim 1, wherein said perfusion lumen is formed from a portion of the guide wire lumen.

4. The catheter as defined in claim 3, wherein a plurality of perfusion ports located distal and proximal to the inflatable region which are in fluid communication with the guide wire lumen form the perfusion lumen of the catheter body.

5. The catheter as defined in claim 1, wherein the inflatable region is configured to center tie radiation source wire within the body lumen so that substantially equal amounts of radiation are directed to the body lumen.

6. The catheter as defined in claim 1, wherein the elongated catheter body has multiple inner lumens extending therethrough and includes an inner lumen for receiving the protective sheath and the radiation source wire.

7. A radiation centering catheter assembly for maintaining the patency of a body lumen for a period of time sufficient to permit delivery of a radiation dose to the body lumen while permitting blood perfusion, comprising:

an elongated catheter body having a proximal end and a distal end;

an inflation lumen extending within the elongated catheter body to a location within a distal portion of the elongated body;

an inflatable region located near the distal end of the elongated catheter body having an interior in fluid communication with the inflation lumen, the inflatable region adapted to be expandable to contact a portion of the body lumen;

a guide wire lumen extending through at least a portion of the elongated catheter body for receiving a guide wire;

a first guide wire port in the distal end of the catheter body in communication with the guide wire lumen and a second guide wire port in the catheter body and spaced a short distance from the distal end of the catheter body and a substantial distance from the proximal end of the catheter body and which is in communication with the guide wire lumen;

an inner lumen extending through the elongated catheter body from the proximal end to about the second guide wire port;

a radiation source wire; and a protective sheath adapted to encase the radiation source wire, the protective sheath and the radiation source wire being insertable within the inner lumen and guide wire lumen to provide a radiation source to the body lumen.

8. The catheter as defined in claim 7, further including a perfusion lumen extending through a portion of the elongated catheter body for permitting perfusion of blood through the inflatable region when the inflatable region is expanded within the body lumen.

9. The catheter of claim 7, wherein the inflatable region is made from a plurality of inflatable balloon segments extending axially along the elongated catheter body.

10. The catheter as defined in claim 8, wherein said perfusion lumen is formed from a portion of the guide wire lumen.

11. The catheter as defined in claim 10, wherein a plurality of perfusion ports located distal and proximal to the inflatable region which are in fluid communication with the guide wire lumen form the perfusion lumen of the catheter body.

12. The catheter as defined in claim 7, wherein the inflatable region is configured to center the radiation source wire within the body lumen so that substantially equal amounts of radiation are directed to the body lumen.

13. The catheter as defined in claim 7, wherein the elongated catheter body has multiple inner lumens extending therethrough and includes an inner lumen for receiving the protective sheath and radiation source wire.

14. A dual therapeutic dilatation catheter assembly for dilating a stenosed region in a body lumen and for maintaining the patency of the body lumen for a period of time sufficient to permit delivery of a radiation dose to the body lumen, comprising:
  an elongated catheter body having a proximal end and a distal end;
  an inflation lumen extending within the elongated catheter body to a location within a distal portion of the elongated body;
  an inflatable region located near the distal end of the elongated catheter body having an interior in fluid communication with the inflation lumen, the inflatable region adapted to be expandable to dilate the stenosed region of the body lumen and to contact a portion of the body lumen;
  a guide wire lumen extending through at least a portion of the elongated catheter body for receiving a guide wire;
  a radiation source wire; and
  a protective sheath adapted to encase the radiation source wire, the protective sheath and the radiation source wire being insertable within the guide wire lumen to provide a radiation source to the body lumen.

15. The catheter as defined in claim 14 further including a perfusion lumen extending through a portion of the elongated catheter body for permitting perfusion of blood through the inflatable region when the inflatable region is expanded within the body lumen.

16. The catheter of claim 14, wherein the inflatable region is made from a plurality of inflatable balloon segments extending axially along the elongated catheter body.

17. The catheter as defined in claim 15, wherein said perfusion lumen is formed from a portion of the guide wire lumen.

18. The catheter as defined in claim 17, wherein a plurality of perfusion ports located distal and proximal to the inflatable region which are in fluid communication with the guide wire lumen form of the perfusion lumen of the catheter body.

19. The catheter as defined in claim 14, wherein the inflatable region is configured to center the radiation source wire within the body lumen so that substantially equal amounts of radiation are directed to the body lumen.

20. The catheter as defined in claim 14, wherein the elongated catheter body has multiple inner lumens extending therethrough and includes an inner lumen for receiving the protective sheath and the radiation source wire.

21. A method for maintaining the patency of a body lumen for a period of time sufficient to permit delivery of a radiation dose to the body lumen while permitting blood perfusion, comprising the steps of:
  a) providing a catheter having:
    an elongated catheter body having a proximal end and a distal end;
    an inflation lumen extending within the elongated catheter body to a location within a distal portion of the elongated body;
    an inflatable region located near the distal end of the elongated catheter body having an interior in fluid communication with the inflation lumen, the inflatable region adapted to be expandable to contact a portion of the body lumen;
    a perfusion lumen extending through a portion of the elongated catheter body for permitting perfusion of blood through the inflatable region when the inflatable region is expanded within the body lumen;
    a guide wire lumen extending through at least a portion of the elongated catheter body for receiving a guide wire;
    a radiation source wire; and
    a protective sheath adapted to encase the radiation source wire, the protective sheath and the radiation source wire being insertable within the guide wire lumen to provide a radiation source to the body lumen;
  b) positioning a guide wire in the body lumen;
  c) advancing the catheter over the guide wire;
  d) advancing the elongated catheter body over the guide wire until the inflatable region is in proper position in the body lumen;
  e) inflating the inflatable region to contact the body lumen to center the guide wire lumen within the body lumen;
  f) perfusing blood flow through the inflatable region;
  g) removing the guide wire from the guide wire lumen;
  h) inserting the protective sheath into the guide wire lumen;
  i) inserting a radiation source wire into the protective sheath and advancing the protective sheath and the radiation source wire to the desired area in the body lumen and administering a radiation dose;
  j) deflating the inflatable region; and
  k) withdrawing the catheter and the protective sheath and the radiation source wire from the body lumen.

22. A method for dilating a stenosed region in a body lumen and maintaining the patency of the body lumen for a period of time sufficient to permit delivery of a radiation dose to the body lumen, comprising the steps of:
  a) providing a catheter having:
    an elongated catheter body having a proximal end and a distal end;
    an inflation lumen extending within the elongated catheter body to a location within a distal portion of the elongated body;
    an inflatable region located near the distal end of the elongated catheter body having an interior in fluid communication with the inflation lumen, the inflatable region adapted to be expandable to dilate the stenosed region of the body lumen and to contact a portion of the body lumen;
    a guide wire lumen extending through at least a portion of the elongated catheter body for receiving a guide wire;

a radiation source wire; and a protective sheath adapted to encase the radiation source wire, the protective sheath and the radiation source wire being insertable within the guide wire lumen to provide a radiation source to the body lumen;

b) positioning a guide wire in the body lumen;

c) advancing the catheter over the guide wire;

d) advancing the elongated catheter body over the guide wire until the inflatable region is in proper position in the body lumen;

e) inflating the inflatable region to dilate the stenosed region in the body lumen;

f) removing the guide wire from the guide wire lumen;

g) inserting the protective sheath into the guide wire lumen;

h) inserting a radiation source wire into the protective sheath and advancing the protective sheath and radiation source wire to the desired area in the body lumen and administering a radiation dose;

i) deflating the inflatable region; and j) withdrawing the catheter and the protective sheath and radiation source wire from the body lumen.

23. The method of claim 22, wherein the catheter further includes a perfusion lumen extending through a portion of the elongated catheter body for permitting perfusion of blood through the inflatable region when the inflatable region is expanded within the body lumen, and further includes, after step (e), the step of perfusing blood flow through the inflatable region.

24. A method for maintaining the patency of a body lumen for a period of time sufficient to permit delivery of a radiation dose to the body lumen while permitting blood perfusion, comprising the steps of:

a) providing a catheter having:
an elongated catheter body having a proximal end and a distal end;
an inflation lumen extending within the elongated catheter body to a location within a distal portion of the elongated body;
an inflatable region located near the distal end of the elongated catheter body having an interior in fluid communication with the inflation lumen, the inflatable region adapted to be expandable to contact a portion of the body lumen;
a guide wire lumen extending through at least a portion of the elongated catheter body for receiving a guide wire;
a first guide wire port in the distal end of the catheter body in communication with the guide wire lumen and a second guide wire port in the distal end of the catheter body which is spaced a short distance from the distal end of the catheter body and a substantial distance from the proximal end of the catheter body and which is in communication with the guide wire lumen;
an inner lumen extending through the elongated catheter body from the proximal end to about the second guide wire port;
a radiation source wire; and
a protective sheath adapted to encase the radiation source wire, the protective sheath and the radiation source wire being insertable within the inner lumen and guide wire lumen to provide a radiation source to the body lumen;

b) preloading the protective sheath within the inner lumen of the elongated catheter using a support mandrel;

c) positioning a guide wire in the body lumen;

d) advancing the catheter over the guide wire;

e) advancing the elongated catheter body over the guide wire until the inflatable region is in proper position in the body lumen;

f) inflating the inflatable region to contact the body lumen to center the guide wire lumen within the body lumen;

g) removing the guide wire from the guide wire lumen;

h) advancing the protective sheath into the guide wire lumen;

i) removing the support mandrel from the protective sheath;

j) inserting a radiation source wire into the protective sheath and advancing the radiation source wire to the desired area in the body lumen and administering a radiation dose;

k) deflating the inflatable region; and l) withdrawing the catheter and the protective sheath and radiation source wire from the body lumen.

25. The method of claim 24, wherein the catheter further includes a perfusion lumen extending through a portion of the elongated catheter body for permitting perfusion of blood through the inflatable region when the inflatable region is expanded within the body lumen, and further includes, after step (f), the step of perfusing blood flow through the inflatable region.

26. A radiation centering catheter assembly for maintaining the patency of a body lumen for a period of time sufficient to permit delivery of a radiation dose to the body lumen while permitting blood perfusion, comprising:

an elongated catheter body having a proximal end and a distal end;

an inflation lumen extending within the elongated catheter body to a location within a distal portion of the elongated body;

an inflatable region located near the distal end of the elongated catheter body having an interior in fluid communication with the inflation lumen, the inflatable region adapted to be expandable to contact a portion of the body lumen;

a perfusion lumen extending through a portion of the elongated catheter body for permitting perfusion of blood through the inflatable region when the inflatable region is expanded within the body lumen;

a guide wire lumen extending through at least a portion of the elongated catheter body for receiving a guide wire; and a protective sheath adapted to encase a radiation source wire, the protective sheath being insertable within the guide wire lumen to provide a barrier between a radiation source wire and body fluids.

27. The catheter of claim 26, wherein the inflatable region is made from a plurality of inflatable balloon segments extending axially along the elongated catheter body.

28. The catheter as defined in claim 26, wherein said perfusion lumen is formed from a portion of the guide wire lumen.

29. The catheter as defined in claim 28, wherein a plurality of perfusion ports located distal and proximal to the inflatable region which are in fluid communication with the guide wire lumen form the perfusion lumen of the catheter body.

30. The catheter as defined in claim 26, wherein the inflatable region is configured to center the protective sheath within the body lumen so that substantially equal amounts of radiation are directed to the body lumen when a radiation source wire is inserted into the protective sheath.

31. The catheter as defined in claim 26, wherein the elongated catheter body has multiple inner lumens extending therethrough and includes an inner lumen for receiving the protective sheath.

32. A radiation centering catheter assembly for maintaining the patency of a body lumen for a period of time sufficient to permit delivery of a radiation dose to the body lumen while permitting blood perfusion, comprising:
  an elongated catheter body having a proximal end and a distal end;
  an inflation lumen extending within the elongated catheter body to a location within a distal portion of the elongated body;
  an inflatable region located near the distal end of the elongated catheter body having an interior in fluid communication with the inflation lumen, the inflatable region adapted to be expandable to contact a portion of the body lumen;
  a guide wire lumen extending through at least a portion of the elongated catheter body for receiving a guide wire;
  a first guide wire port in the distal end of the catheter body in communication with the guide wire lumen and a second guide wire port in the catheter body and spaced a short distance from the distal end of the catheter body and a substantial distance from the proximal end of the catheter body and which is in communication with the guide wire lumen;
  an inner lumen extending through the elongated catheter body from the proximal end to about the second guide wire port; and
  a protective sheath adapted to encase a radiation source wire, the protective sheath being insertable within the inner lumen and guide wire lumen to provide a barrier between a radiation source wire and body fluids.

33. The catheter as defined in claim 32, further including a perfusion lumen extending through a portion of the elongated catheter body for permitting perfusion of blood through the inflatable region when the inflatable region is expanded within the body lumen.

34. The catheter of claim 32, wherein the inflatable region is made from a plurality of inflatable balloon segments extending axially along the elongated catheter body.

35. The catheter as defined in claim 33, wherein said perfusion lumen is formed from a portion of the guide wire lumen.

36. The catheter as defined in claim 35, wherein a plurality of perfusion ports located distal and proximal to the inflatable region which are in fluid communication with the guide wire lumen form the perfusion lumen of the catheter body.

37. The catheter as defined in claim 32, wherein the inflatable region is configured to center the protective sheath within the body lumen so that substantially equal amounts of radiation are directed to the body lumen when a radiation source wire is inserted into the protective sheath.

38. The catheter as defined in claim 32, wherein the elongated catheter body has multiple inner lumens extending therethrough and includes an inner lumen for receiving the protective sheath.

39. A dual therapeutic dilatation catheter assembly for dilating a stenosed region in a body lumen and for maintaining the patency of the body lumen for a period of time sufficient to permit delivery of a radiation dose to the body lumen, comprising:
  an elongated catheter body having a proximal end and a distal end;
  an inflation lumen extending within the elongated catheter body to a location within a distal portion of the elongated body;
  an inflatable region located near the distal end of the elongated catheter body having an interior in fluid communication with the inflation lumen, the inflatable region adapted to be expandable to dilate the stenosed region of the body lumen and to contact a portion of the body lumen;
  a guide wire lumen extending through at least a portion of the elongated catheter body for receiving a guide wire; and
  a protective sheath adapted to encase a radiation source wire, the protective sheath being insertable within the guide wire lumen to provide a barrier between a radiation source wire and body fluids.

40. The catheter as defined in claim 39 further including a perfusion lumen extending through a portion of the elongated catheter body for permitting perfusion of blood through the inflatable region when the inflatable region is expanded within the body lumen.

41. The catheter of claim 39, wherein the inflatable region is made from a plurality of inflatable balloon segments extending axially along the elongated catheter body.

42. The catheter as defined in claim 40, wherein said perfusion lumen is formed from a portion of the guide wire lumen.

43. The catheter as defined in claim 42, wherein a plurality of perfusion ports located distal and proximal to the inflatable region which are in fluid communication with the guide wire lumen form of the perfusion lumen to the catheter body.

44. The catheter as defined in claim 39, wherein the inflatable region is configured to center the protective sheath within the body lumen so that substantially equal amounts of radiation are directed to the body lumen when a radiation source wire is inserted into the protective sheath.

45. The catheter as defined in claim 39, wherein the elongated catheter body has multiple inner lumens extending therethrough and includes an inner lumen for receiving the protective sheath.

46. A method for maintaining the patency of a body lumen for a period of time sufficient to permit delivery of a radiation dose to the body lumen while permitting blood perfusion, comprising the steps of:
  d) providing a catheter having:
    an elongated catheter body having a proximal end and a distal end;
    an inflation lumen extending within the elongated catheter body to a location within a distal portion of the elongated body;
    an inflatable region located near the distal end of the elongated catheter body having an interior in fluid communication with the inflation lumen, the inflatable region adapted to be expandable to contact a portion of the body lumen;
    a perfusion lumen extending through a portion of the elongated catheter body for permitting perfusion of blood through the inflatable region when the inflatable region is expanded within the body lumen;
    a guide wire lumen extending through at least a portion of the elongated catheter body for receiving a guide wire; and a protective sheath adapted to encase a radiation source wire, the protective sheath being insertable within the guide wire lumen to provide a barrier between a radiation source wire and body fluids;

e) positioning a guide wire in the body lumen;

f) advancing the catheter over the guide wire;

d) advancing the elongated catheter body over the guide wire until the inflatable region is in proper position in the body lumen;

e) inflating the inflatable region to contact the body lumen to center the guide wire lumen within the body lumen;

f) perfusing blood flow through the inflatable region;

i) removing the guide wire from the guide wire lumen;

j) inserting the protective sheath into the guide wire lumen;

i) inserting a radiation source wire into the protective sheath and advancing the protective sheath and radiation source wire to the desired area in the body lumen and administering a radiation dose;

j) deflating the inflatable region; and k) withdrawing the catheter and the protective sheath and radiation source wire from the body lumen.

47. A method for dilating a stenosed region in a body lumen and maintaining the patency of the body lumen for a period of time sufficient to permit delivery of a radiation dose to the body lumen, comprising the steps of:

b) providing a catheter having:
an elongated catheter body having a proximal end and a distal end;
an inflation lumen extending within the elongated catheter body to a location within a distal portion of the elongated body;
an inflatable region located near the distal end of the elongated catheter body having an interior in fluid communication with the inflation lumen, the inflatable region adapted to be expandable to dilate the stenosed region of the body lumen and to contact a portion of the body lumen;
a guide wire lumen extending through at least a portion of the elongated catheter body for receiving a guide wire; and
a protective sheath adapted to encase a radiation source wire, the protective sheath being insertable within the guide wire lumen to provide a barrier between a radiation source wire and body fluids;

b) positioning a guide wire in the body lumen;

c) advancing the catheter over the guide wire;

d) advancing the elongated catheter body over the guide wire until the inflatable region is in proper position in the body lumen;

e) inflating the inflatable region to dilate the stenosed region in the body lumen;

f) removing the guide wire from the guide wire lumen;

h) inserting the protective sheath into the guide wire lumen;

h) inserting a radiation source wire into the protective sheath and advancing the protective sheath and radiation source wire to the desired area in the body lumen and administering a radiation dose;

i) deflating the inflatable region; and j) withdrawing the catheter and the protective sheath and radiation source wire from the body lumen.

48. The method of claim 47, wherein the catheter further includes a perfusion lumen extending through a portion of the elongated catheter body for permitting perfusion of blood through the inflatable region when the inflatable region is expanded within the body lumen, and further includes, after step (e) the step of perfusing blood flow through the inflatable region.

49. A method for maintaining the patency of a body lumen for a period of time sufficient to permit delivery of a radiation dose to the body lumen while permitting blood perfusion, comprising the steps of:

b) providing a catheter having:
an elongated catheter body having a proximal end and a distal end;
an inflation lumen extending within the elongated catheter body to a location within a distal portion of the elongated body;
an inflatable region located near the distal end of the elongated catheter body having an interior in fluid communication with the inflation lumen, the inflatable region adapted to be expandable to contact a portion of the body lumen;
a guide wire lumen extending through at least a portion of the elongated catheter body for receiving a guide wire;
a first guide wire port in the distal end of the catheter body in communication with the guide wire lumen and a second guide wire port in the distal end of the catheter body which is spaced a short distance from the distal end of the catheter body and a substantial distance from the proximal end of the catheter body and which is in communication with the guide wire lumen;
an inner lumen extending through the elongated catheter body from the proximal end to about the second guide wire port; and
a protective sheath adapted to encase a radiation source wire, the protective sheath being insertable within the inner lumen and guide wire lumen to provide a barrier between a radiation source wire and body fluids;

b) preloading the protective sheath within the inner lumen of the elongated catheter using a support mandrel;

c) positioning a guide wire in the body lumen;

d) advancing the catheter over the guide wire;

e) advancing the elongated catheter body over the guide wire until the inflatable region is in proper position in the body lumen;

f) inflating the inflatable region to contact the body lumen to center the guide wire lumen within the body lumen;

j) removing the guide wire from the guide wire lumen;

k) advancing the protective sheath into the guide wire lumen;

l) removing the support mandrel from the protective sheath;

j) inserting a radiation source wire into the protective sheath and advancing the radiation source wire to the desired area in the body lumen and administering a radiation dose;

k) deflating the inflatable region; and l) withdrawing the catheter and the protective sheath and radiation source wire from the body lumen.

50. The method of claim 49, wherein the catheter further includes a perfusion lumen extending through a portion of the elongated catheter body for permitting perfusion of blood through the inflatable region when the inflatable region is expanded within the body lumen, and further includes, after step (f), the step of perfusing blood flow through the inflatable region.

* * * * *